(12) United States Patent
Belson et al.

(10) Patent No.: US 9,162,037 B2
(45) Date of Patent: *Oct. 20, 2015

(54) INTRAVENOUS CATHETER INSERTION DEVICE AND METHOD OF USE

(75) Inventors: Amir Belson, Los Altos, CA (US); Gregory W. Hall, Redwood City, CA (US); Scott A. Daniel, Hayward, CA (US); Robert Brommer, Hayward, CA (US)

(73) Assignee: Vascular Pathways, Inc., Salt Lake City, UT (US)

( * ) Notice: Subject to any disclaimer, the term of this patent is extended or adjusted under 35 U.S.C. 154(b) by 683 days.
This patent is subject to a terminal disclaimer.

(21) Appl. No.: 11/577,491

(22) PCT Filed: Jul. 6, 2006

(86) PCT No.: PCT/US2006/026671
§ 371 (c)(1),
(2), (4) Date: Aug. 20, 2008

(87) PCT Pub. No.: WO2007/006055
PCT Pub. Date: Jan. 11, 2007

(65) Prior Publication Data
US 2008/0300574 A1 Dec. 4, 2008

Related U.S. Application Data

(60) Provisional application No. 60/697,333, filed on Jul. 6, 2005.

(51) Int. Cl.
*A61M 25/06* (2006.01)
*A61M 25/09* (2006.01)
(Continued)

(52) U.S. Cl.
CPC ....... *A61M 25/0606* (2013.01); *A61M 25/0631* (2013.01); *A61M 25/09* (2013.01);
(Continued)

(58) Field of Classification Search
CPC ............. A61M 25/0631; A61M 25/0606; A61M 5/3232; A61M 25/09; A61M 5/3243; A61M 25/01; A61M 5/3257; A61M 25/065; A61M 5/3234

USPC ............. 604/95.01, 156, 157, 159, 164.01, 604/164.09, 164.1, 164.11, 164.12, 164.13, 604/507, 508, 510; 600/585
See application file for complete search history.

(56) References Cited

U.S. PATENT DOCUMENTS

| 3,572,334 A | 3/1971 | Petterson |
| 3,592,192 A | 7/1971 | Harautuneian |

(Continued)

FOREIGN PATENT DOCUMENTS

| EP | 0515710 A1 | 12/1992 |
| EP | 0567321 A2 | 10/1993 |

(Continued)

OTHER PUBLICATIONS

European office action dated Apr. 21, 2008 for EP Application No. 06800027.2.

(Continued)

*Primary Examiner* — Theodore Stigell
*Assistant Examiner* — Lauren M Peng
(74) *Attorney, Agent, or Firm* — Rutan & Tucker, LLP

(57) ABSTRACT

An intravenous catheter insertion device and method of use are described. The insertion device coordinates movement of an access needle, a coaxial intravenous catheter and a flexible safety guidewire. A vein is punctured with the access needle, then an actuation member on the insertion device is used to advance the safety guidewire into the vein. The safety guidewire allows the access needle and the intravenous catheter to be safely advanced into the vein. Then, the actuation member is actuated to simultaneously withdraw the access needle and the safety guidewire, leaving only the intravenous catheter in the vein. The intravenous catheter is then disconnected from the insertion device and connected to a source of intravenous fluid, medication, etc.

20 Claims, 9 Drawing Sheets

(51) Int. Cl.
*A61M 5/32* (2006.01)
*A61M 25/01* (2006.01)

(52) U.S. Cl.
CPC ........... *A61M 5/3232* (2013.01); *A61M 5/3234* (2013.01); *A61M 5/3243* (2013.01); *A61M 5/3257* (2013.01); *A61M 25/01* (2013.01); *A61M 25/065* (2013.01)

(56) References Cited

U.S. PATENT DOCUMENTS

| | | |
|---|---|---|
| 3,610,240 A | 10/1971 | Harautuneian |
| 4,027,668 A | 6/1977 | Dunn |
| 4,037,600 A | 7/1977 | Poncy et al. |
| 4,292,970 A | 10/1981 | Hession, Jr. |
| 4,345,602 A | 8/1982 | Yoshimura et al. |
| 4,417,886 A | 11/1983 | Frankhouser et al. |
| 4,509,945 A | 4/1985 | Kramann et al. |
| 4,747,831 A * | 5/1988 | Kulli ........................... 604/110 |
| 4,798,193 A | 1/1989 | Giesy et al. |
| 4,813,934 A | 3/1989 | Engelson et al. |
| 4,834,718 A | 5/1989 | McDonald |
| 4,900,307 A | 2/1990 | Kulli |
| 4,909,793 A | 3/1990 | Vining et al. |
| 4,917,102 A | 4/1990 | Miller et al. |
| 4,944,725 A | 7/1990 | McDonald |
| 4,944,728 A | 7/1990 | Carrell et al. |
| 4,966,589 A | 10/1990 | Kaufman et al. |
| 5,007,901 A | 4/1991 | Shields |
| 5,019,049 A | 5/1991 | Haining |
| 5,047,013 A | 9/1991 | Rossdeutscher |
| 5,054,501 A | 10/1991 | Chuttani et al. |
| 5,176,650 A | 1/1993 | Haining |
| 5,246,426 A * | 9/1993 | Lewis et al. ............... 604/168.01 |
| 5,338,311 A | 8/1994 | Mahurkar |
| 5,366,441 A | 11/1994 | Crawford |
| 5,456,668 A | 10/1995 | Ogle, II |
| 5,501,675 A | 3/1996 | Erskine et al. |
| 5,512,052 A * | 4/1996 | Jesch ........................... 604/158 |
| 5,562,629 A | 10/1996 | Haughton et al. |
| 5,562,634 A | 10/1996 | Flumene et al. |
| 5,573,510 A | 11/1996 | Isaacson |
| 5,630,823 A | 5/1997 | Schmitz-Rode et al. |
| 5,695,474 A | 12/1997 | Daugherty |
| 5,704,914 A * | 1/1998 | Stocking et al. .......... 604/164.07 |
| 5,722,425 A * | 3/1998 | Bostrom ........................ 600/585 |
| 5,749,371 A | 5/1998 | Zadini et al. |
| 5,750,741 A | 5/1998 | Crocker et al. |
| 5,800,395 A | 9/1998 | Botich et al. |
| 5,865,806 A * | 2/1999 | Howell ...................... 604/164.12 |
| 5,891,098 A | 4/1999 | Huang |
| 5,891,105 A | 4/1999 | Mahurkar |
| 5,895,398 A | 4/1999 | Wensel et al. |
| 5,941,854 A | 8/1999 | Bhitiyakul |
| 5,944,690 A | 8/1999 | Falwell |
| 5,989,271 A | 11/1999 | Bonnette et al. |
| 5,997,507 A | 12/1999 | Dysarz |
| 6,019,736 A | 2/2000 | Avellanet |
| 6,056,726 A | 5/2000 | Isaacson |
| 6,083,237 A | 7/2000 | Huitema et al. |
| 6,139,557 A | 10/2000 | Passafaro et al. |
| 6,171,234 B1 * | 1/2001 | White et al. .................... 600/102 |
| 6,193,690 B1 | 2/2001 | Dysarz |
| 6,197,001 B1 | 3/2001 | Wilson et al. |
| 6,221,047 B1 | 4/2001 | Greene et al. |
| 6,322,537 B1 | 11/2001 | Chang |
| 6,325,781 B1 * | 12/2001 | Takagi et al. ................. 604/198 |
| 6,406,442 B1 | 6/2002 | McFann et al. |
| 6,436,070 B1 | 8/2002 | Botich et al. |
| 6,436,112 B2 | 8/2002 | Wensel et al. |
| 6,485,497 B2 | 11/2002 | Wensel et al. |
| 6,530,935 B2 | 3/2003 | Wensel et al. |
| 6,547,762 B1 | 4/2003 | Botich et al. |
| 6,620,136 B1 | 9/2003 | Pressly, Sr. et al. |
| 6,689,102 B2 | 2/2004 | Greene |
| 6,692,508 B2 | 2/2004 | Wensel et al. |
| 6,692,509 B2 | 2/2004 | Wensel et al. |
| 6,695,814 B2 | 2/2004 | Greene et al. |
| 6,711,444 B2 | 3/2004 | Koblish |
| 6,730,062 B2 | 5/2004 | Hoffman et al. |
| 6,740,096 B2 | 5/2004 | Teague et al. |
| 6,745,080 B2 | 6/2004 | Koblish |
| 6,776,788 B1 | 8/2004 | Klint et al. |
| 6,824,545 B2 | 11/2004 | Sepetka et al. |
| 6,921,386 B2 | 7/2005 | Shue et al. |
| 6,921,391 B1 | 7/2005 | Barker et al. |
| 6,929,624 B1 | 8/2005 | Del Castillo |
| 6,939,325 B2 | 9/2005 | Haining |
| 6,942,652 B1 | 9/2005 | Pressly, Sr. et al. |
| 6,953,448 B2 | 10/2005 | Moulton et al. |
| 6,958,054 B2 | 10/2005 | Fitzgerald |
| 7,044,935 B2 | 5/2006 | Shue et al. |
| 7,381,205 B2 | 6/2008 | Thommen |
| 7,776,052 B2 | 8/2010 | Greenberg et al. |
| 8,728,035 B2 | 5/2014 | Warring et al. |
| 2001/0014786 A1 | 8/2001 | Greene et al. |
| 2002/0107526 A1 | 8/2002 | Greenberg et al. |
| 2002/0165497 A1 | 11/2002 | Greene et al. |
| 2003/0060760 A1 | 3/2003 | Botich et al. |
| 2003/0073956 A1 | 4/2003 | Hoffman et al. |
| 2003/0204186 A1 | 10/2003 | Geistert |
| 2004/0106903 A1 | 6/2004 | Shue et al. |
| 2004/0267204 A1 | 12/2004 | Brustowicz |
| 2005/0010095 A1 | 1/2005 | Stewart et al. |
| 2005/0027256 A1 * | 2/2005 | Barker et al. ............ 604/164.12 |
| 2005/0033137 A1 | 2/2005 | Oral et al. |
| 2005/0075606 A1 * | 4/2005 | Botich et al. .................. 604/110 |
| 2005/0107769 A1 | 5/2005 | Thommen |
| 2005/0119619 A1 | 6/2005 | Haining |
| 2005/0165355 A1 | 7/2005 | Fitzgerald |
| 2007/0179446 A1 | 8/2007 | Carrez et al. |
| 2007/0244438 A1 | 10/2007 | Perez |
| 2010/0094310 A1 | 4/2010 | Warring et al. |
| 2015/0038943 A1 | 2/2015 | Warring et al. |

FOREIGN PATENT DOCUMENTS

| | | |
|---|---|---|
| EP | 0567321 A3 | 5/1994 |
| EP | 0750916 A2 | 1/1997 |
| EP | 0750916 A3 | 2/1997 |
| EP | 0832663 A2 | 4/1998 |
| EP | 0832663 A3 | 5/1998 |
| EP | 0910988 A1 | 4/1999 |
| EP | 0800790 B1 | 7/1999 |
| EP | 0652020 B1 | 12/1999 |
| EP | 1378263 A | 1/2004 |
| EP | 0942761 B1 | 6/2004 |
| EP | 1075850 B1 | 9/2004 |
| EP | 1457229 A1 | 9/2004 |
| EP | 0778043 B1 | 11/2005 |
| EP | 1611916 A1 | 1/2006 |
| JP | 2004-223252 A | 8/2004 |
| JP | 2005137888 A2 | 6/2005 |
| WO | WO 83/01575 A | 5/1983 |
| WO | WO9222344 A1 | 12/1992 |
| WO | WO9519193 A1 | 7/1995 |
| WO | WO9523003 A1 | 8/1995 |
| WO | WO9632981 A1 | 10/1996 |
| WO | WO9705912 A2 | 2/1997 |
| WO | WO 97/05912 A3 | 3/1997 |
| WO | WO9721458 A1 | 6/1997 |
| WO | WO9824494 A1 | 6/1998 |
| WO | WO0006226 A1 | 2/2000 |
| WO | WO0012160 A1 | 3/2000 |
| WO | WO0047256 A1 | 8/2000 |
| WO | WO03043686 A1 | 5/2003 |
| WO | WO03047675 A2 | 6/2003 |
| WO | WO 03/047675 A3 | 10/2003 |
| WO | WO 2004/018031 A2 | 3/2004 |
| WO | WO 2004/018031 A3 | 4/2004 |
| WO | WO2005074412 A2 | 8/2005 |
| WO | WO2005087306 A1 | 9/2005 |

(56) References Cited

FOREIGN PATENT DOCUMENTS

| WO | WO 2005/074412 A3 | 2/2006 |
| WO | WO2007006055 | 1/2007 |
| WO | WO 2007/006055 A3 | 7/2007 |

OTHER PUBLICATIONS

European office action dated Aug. 6, 2012 for EP Application No. 07783404.2.
European office action dated Oct. 5, 2010 for EP Application No. 07783404.2.
European search report and opinion dated Jul. 10, 2009 for EP Application No. 07783404.2.
International search report and written opinion dated Jun. 1, 2007 for PCT/US2006/026671.
International search report and written opinion dated Oct. 23, 2008 for PCT/US2007/068393.
Office action dated Oct. 25, 2010 for U.S. Appl. No. 12/307,519.
Office action dated Mar. 10, 2011 for U.S. Appl. No. 12/307,519.
Office action dated Nov. 14, 2013 for U.S. Appl. No. 12/307,519.
U.S. Appl. No. 14/250,093, filed Apr. 10, 2014, Warring et al.
Notice of allowance dated Jan. 29, 2014 for U.S. Appl. No. 12/307,519.

* cited by examiner

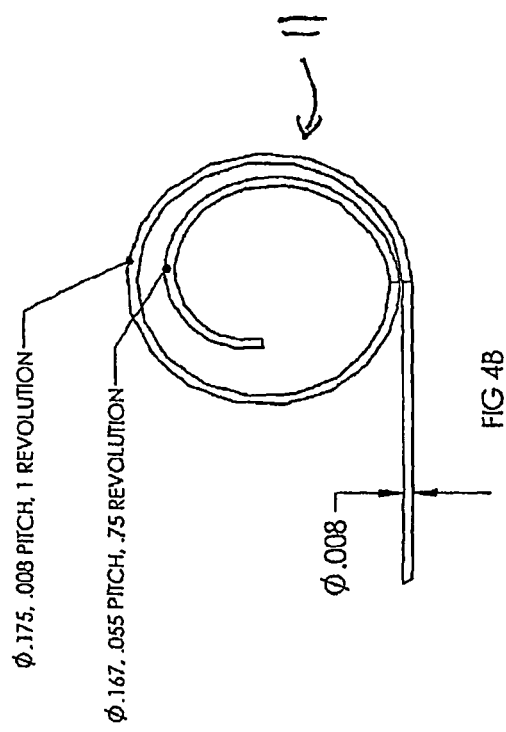
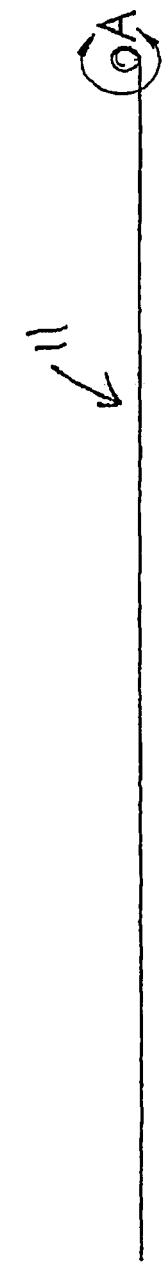

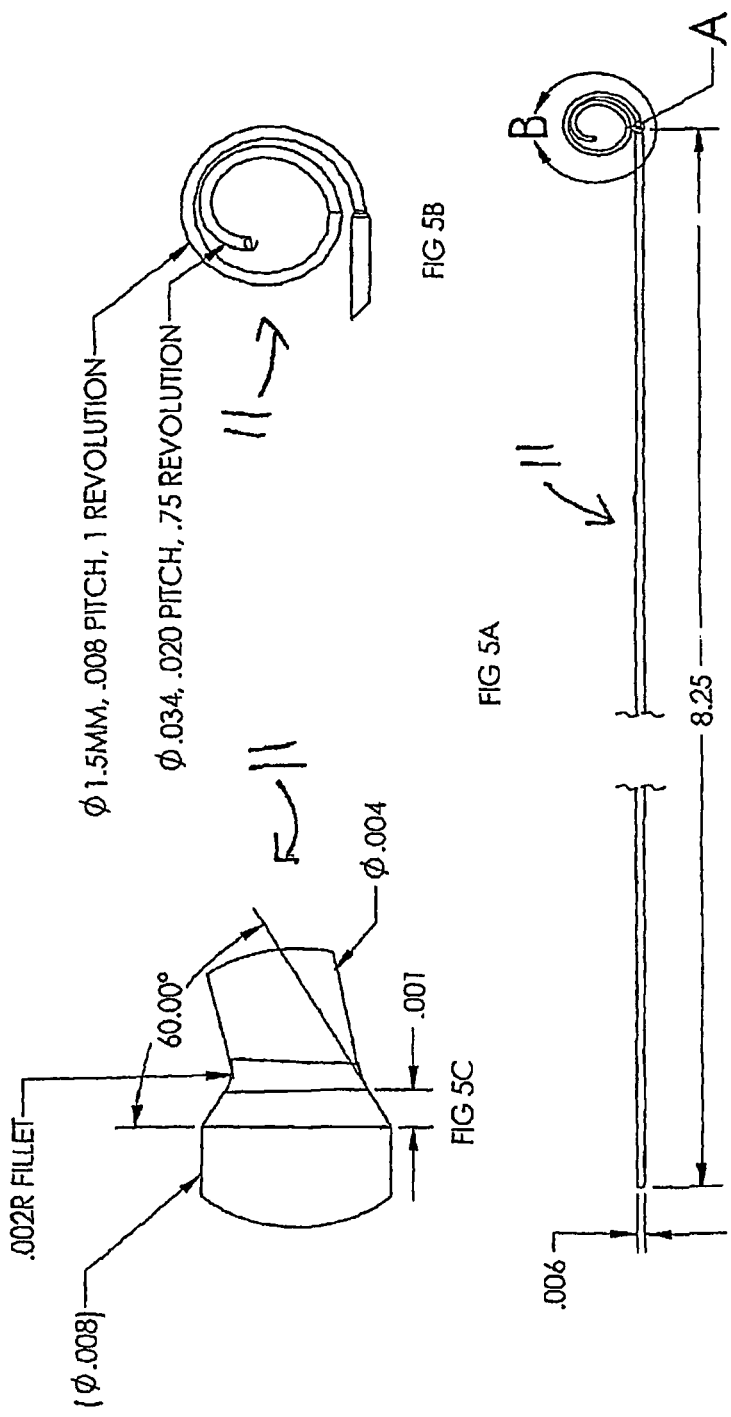

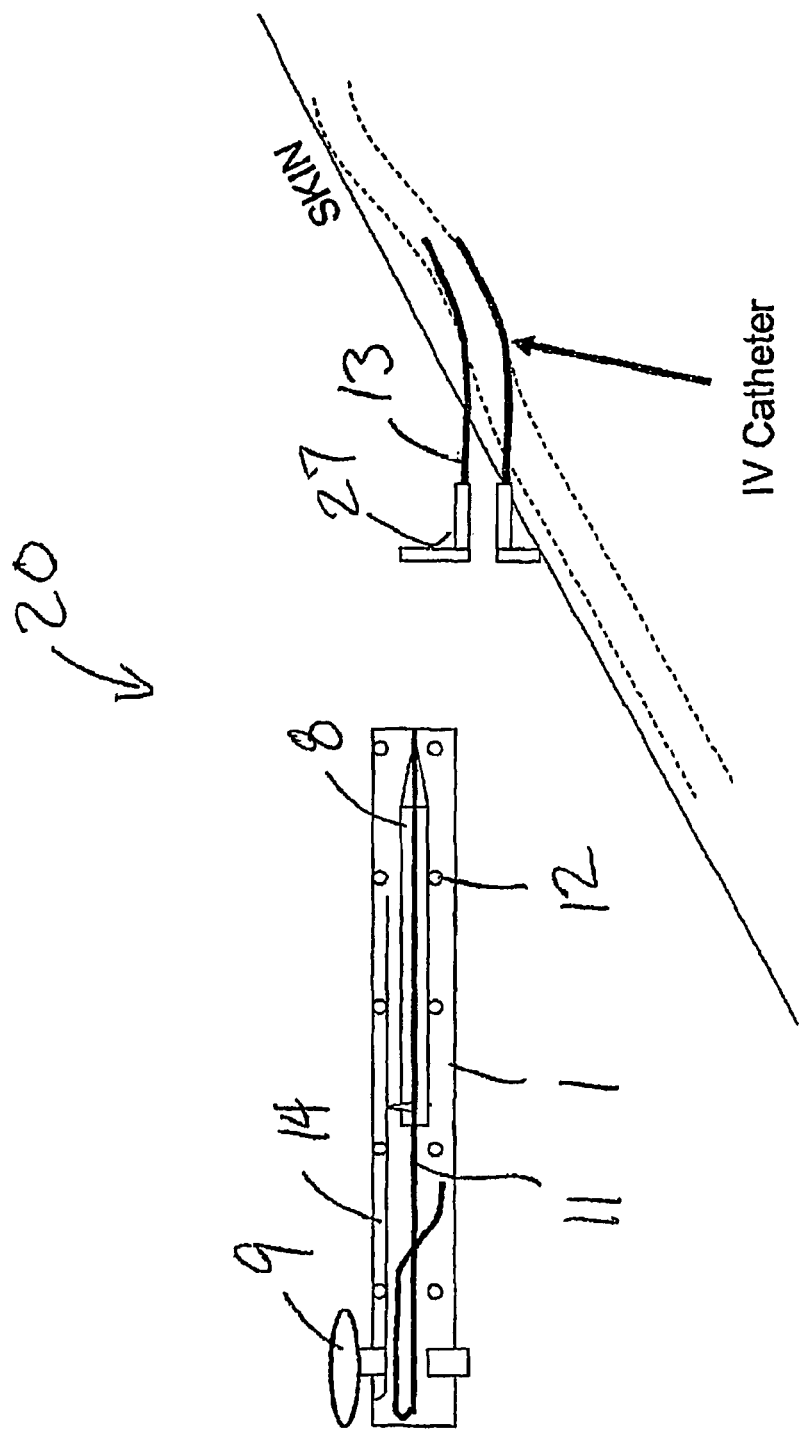

INTRAVENOUS CATHETER INSERTION DEVICE AND METHOD OF USE

CROSS REFERENCE TO RELATED APPLICATIONS

This application is a U.S. national stage application under 35 USC §371 of International Application No. PCT/US2006/026671, filed Jul. 6, 2006, which claims the benefit of priority to U.S. Provisional Patent Application No. 60/697,333, filed Jul. 6, 2005 each of which is incorporated by reference in its entirety into this application.

FIELD OF THE INVENTION

The present invention relates to devices and methods for insertion and placement of an intravenous catheter into a vein or artery of a patient. The devices and methods of the invention facilitate safe placement of the catheter into the patient's vein or artery, which is of particular importance in the case of small, tortuous, collapsed, fragile, and/or difficult to locate vessels. The devices and methods also provide protection against accidental punctures and/or contamination by the needle after placement of the intravenous catheter.

BACKGROUND OF THE INVENTION

The following patents describe prior intravenous catheter insertion devices and/or safety devices for syringes and needles.

Haining—EP00515710A1 Intravenous catheter and insertion device
Haining—EP00515710B1 Intravenous catheter and insertion device
Haining—U.S. Pat. No. 5,019,049 Intravenous catheter and insertion device
Haining—U.S. Pat. No. 5,176,650 Intravenous catheter and insertion device
Chang—EP00567321A2 Intravenous catheter with needle guard
Mahurkar—EP00652020B1 Retractable hypodermic needle assembly
Mahurkar—EP00910988A1 Blood sample collection assembly
Mahurkar—U.S. Pat. No. 5,891,105 Hypodermic needle assembly
DeWitt—U.S. Pat. No. 3,572,334 Intravenous catheter placement unit
van Heugten—EP00750916A2 Protective needle cover containment
Botich—EP00942761B1 Medical device with retractable needle
Botich—EP01075850B1 Apparatus for intravenous catheter insertion
Botich et al—U.S. Pat. No. 5,800,395 Medical device with retractable needle
Botich et al—U.S. Pat. No. 6,436,070 Catheter insertion device with retractable needle
Botich et al—US23060760A1 Catheter insertion device with retractable needle
Botich et al—WO00012160A1 Fluid infusion device with retractable needle
Botich—WO09632981A1 Safety stylet for intravenous catheter insertion
Botich—WO09824494A1 Medical device with retractable needle
Shue—EP01457229A1 Intravenous catheter inserting device
Shue—US24106903A1 Intravenous catheter inserting device
Harautuneian—U.S. Pat. No. 3,592,192 Intravenous catheter apparatus with catheter telescoped on outside of puncturing cannula
Harautuneian—U.S. Pat. No. 3,610,240 Intravenous catheter apparatus with catheter telescoped inside puncturing cannula
Poncy et al—U.S. Pat. No. 4,037,600 Catheter placement system
Hession—U.S. Pat. No. 4,292,970 Apparatus for intravenous catheter starter
McDonald—U.S. Pat. No. 4,834,718 Safety needle apparatus
McDonald—U.S. Pat. No. 4,944,725 Safety needle apparatus
Vining et al—U.S. Pat. No. 4,909,793 Intravenous catheter apparatus with retractable stylet
Carrell et al—U.S. Pat. No. 4,944,728 Intravenous catheter placement device
Kaufman—U.S. Pat. No. 4,966,589 Intravenous catheter placement device
Shields—U.S. Pat. No. 5,007,901 Intravenous catheter insertion device
Haughton et al—U.S. Pat. No. 5,562,629 Catheter placement system utilizing a handle, a sharp, and a releasable retainer mechanism providing retraction of the sharp upon disengagement of the catheter from the handle
Flumene et al—U.S. Pat. No. 5,562,634 Intravenous catheter with automatically retracting needle-guide
Isaacson—U.S. Pat. No. 5,573,510 Safety intravenous catheter assembly with automatically retractable needle
Isaacson—U.S. Pat. No. 6,056,726 Self-contained safety intravenous catheter insertion device
Isaacson—WO09523003A1 Self-contained safety intravenous catheter insertion device
Huang—U.S. Pat. No. 5,891,098 Safety intravenous catheter
Bhitiyakul—U.S. Pat. No. 5,941,854 Intravenous catheter
Dysarz—U.S. Pat. No. 5,997,507 Biased spring hard needle retractable IV catheter
Dysarz—U.S. Pat. No. 6,193,690 Inclined plane latching device for an IV catheter
Greene et al—U.S. Pat. No. 6,221,047 Safety intravenous catheter assembly and method for use with a needle
Greene et al—U.S. Pat. No. 6,689,102 Safety intravenous catheter assembly
Greene et al—U.S. Pat. No. 6,695,814 Safety intravenous catheter assembly and method for use with a needle
Greene et al—US21014786A1 Safety intravenous catheter assembly and method for use with a needle
Greene et al—US22165497A1 Safety intravenous catheter assembly
Greene et al—WO00006226A1 Safety intravenous catheter assembly and method for use with a needle
Chang—U.S. Pat. No. 6,322,537 Safety intravenous catheter
Pressly, Sr. et al—U.S. Pat. No. 6,620,136 Retractable I-V catheter placement device
Pressly, Sr. et al—WO00047256A1 Retractable I-V catheter placement device
Hoffman et al—U.S. Pat. No. 6,730,062 Safety catheter with non-removable retractable needle
Hoffman et al—US23073956A1 Safety catheter with non-removable retractable needle
Brustowicz—US24267204A1 On-demand needle retaining and locking mechanism for use in intravenous catheter assemblies
Garcia Andreo—WO03043686A1 Flow regulating/autovalve intravenous catheter Sircom—WO09222344A1 Needle guard for intravenous catheter placement Ogle—WO09519193A1 Retractable venipuncture catheter needle and receptacle Rohrbough et al—WO09705912A2 Retractable venipuncture catheter needle and receptacle Hwang—WO09721458A1 Intravenous catheter with flexible extender and protector against needle tip

SUMMARY OF THE INVENTION

In one aspect, the present invention takes the form of an intravenous catheter insertion device that provides coordinated movement of an access needle, an intravenous catheter and a safety guidewire. The device holds the access needle and the intravenous catheter in a coaxial arrangement for puncturing a vein or other target vessel. A blood flashback chamber provides a visual indication that the tip of the needle is in the lumen of the vein. Upon vein puncture by the access needle, a flexible safety guidewire is advanced through the access needle into the lumen of the vein using an actuation member located on the exterior of the device. With the flexible safety guidewire deployed within the lumen of the vein, the access needle and the intravenous catheter can be safely advanced into the vein until the tip of the intravenous catheter is also within the lumen of the vein. Alternatively, the intravenous catheter can be advanced separately while holding the access needle stationary. Then, the actuation member is actuated to simultaneously withdraw the access needle and the safety guidewire. Preferably, the access needle and the safety guidewire are withdrawn automatically by the action of a spring or other biasing member, leaving only the intravenous catheter in the vein. Once the access needle and the safety guidewire have been withdrawn, the intravenous catheter can be disconnected from the insertion device and connected to a source of intravenous fluid, medication, etc.

In another aspect, the present invention provides an improved method for insertion and placement of an intravenous catheter. The method includes the steps of: puncturing a vein or other target vessel with an access needle arranged coaxially with an intravenous catheter; verifying the location of the access needle tip in the lumen of the vein; advancing a safety guidewire through the access needle into the lumen of the vein, advancing the tip of the intravenous catheter into the vein; and simultaneously withdrawing the access needle and the safety guidewire from the intravenous catheter and from the patient.

Although the invention is described in relation to insertion of an intravenous catheter, the apparatus and methods described herein could readily be adapted for insertion of any catheter or similar device into a vein, artery or other internal body structure.

BRIEF DESCRIPTION OF THE DRAWINGS

In the drawings.

FIGS. 4A and 4B are detail drawings of a safety guidewire for use with the intravenous catheter insertion device.

FIGS. 5A, 5B and 5C are detail drawings of another safety guidewire for use with the intravenous catheter insertion device.

FIGS. 7-9 illustrate a method of intravenous catheter insertion according to the present invention.

DETAILED DESCRIPTION OF THE INVENTION

Figure 1:
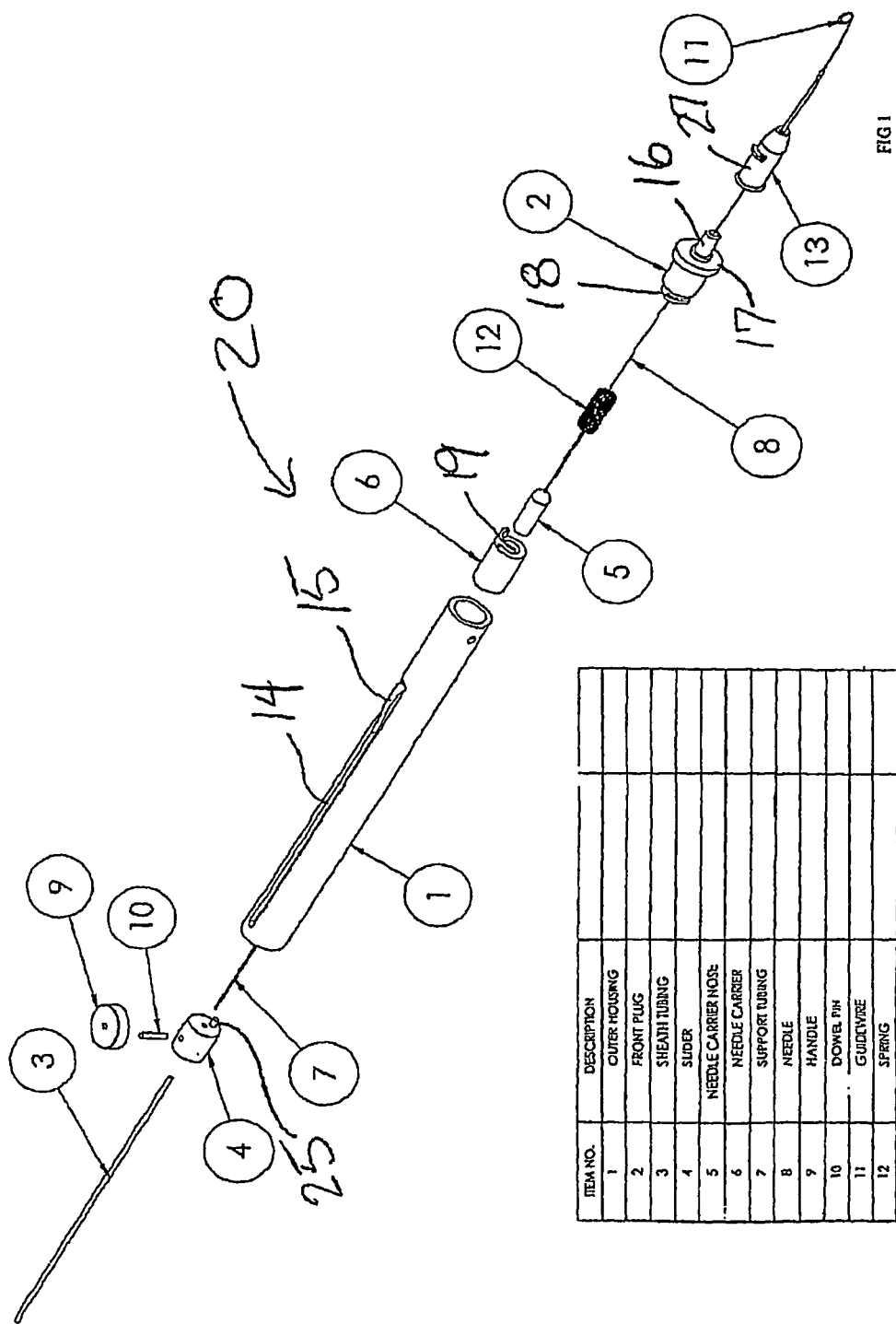
FIG. 1 shows an exploded view of an intravenous catheter insertion device according to the present invention.
Figure 2:
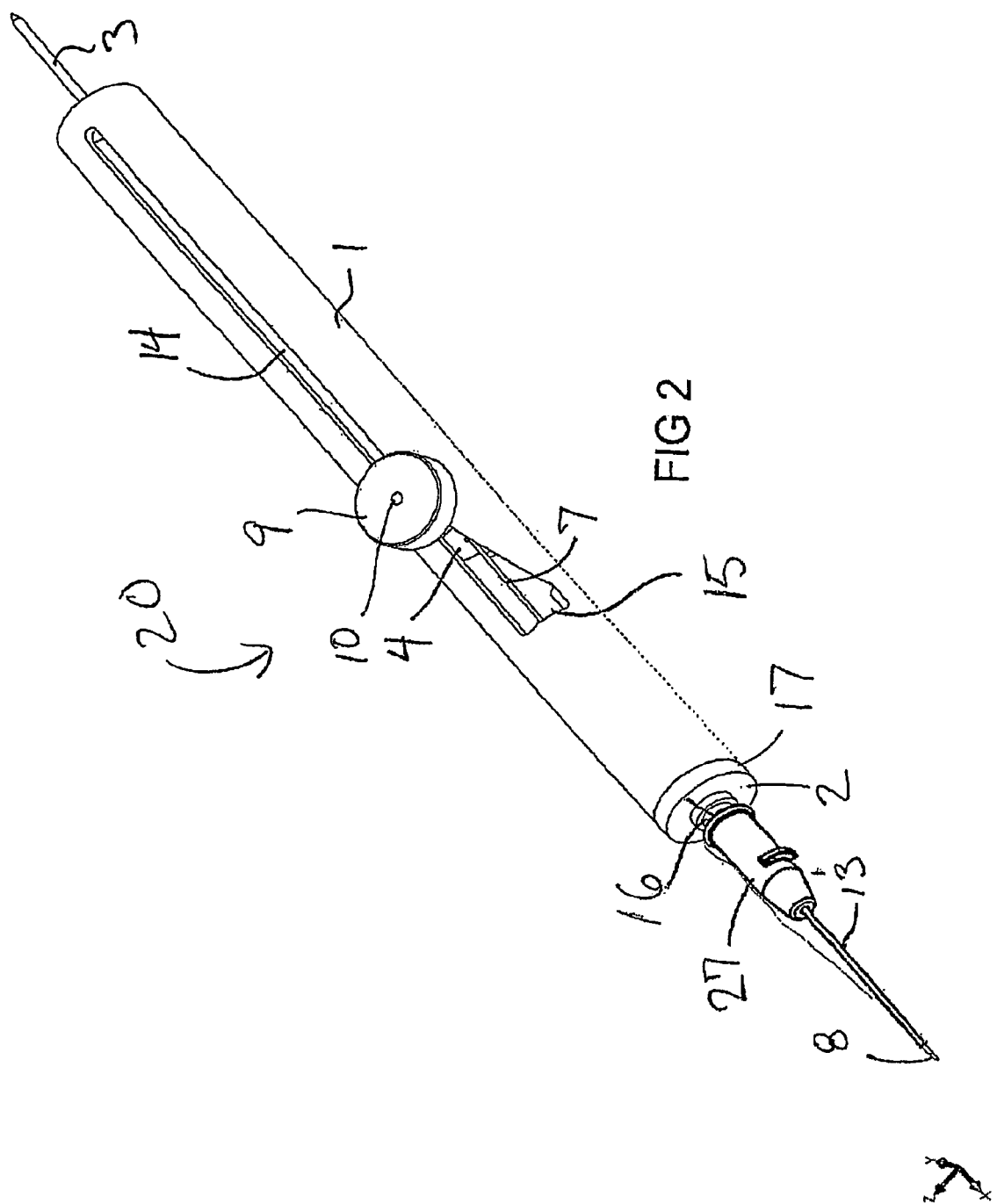
FIG. 2 shows an assembly drawing of the intravenous catheter insertion device in an undeployed state, ready for use.
Figure 3:
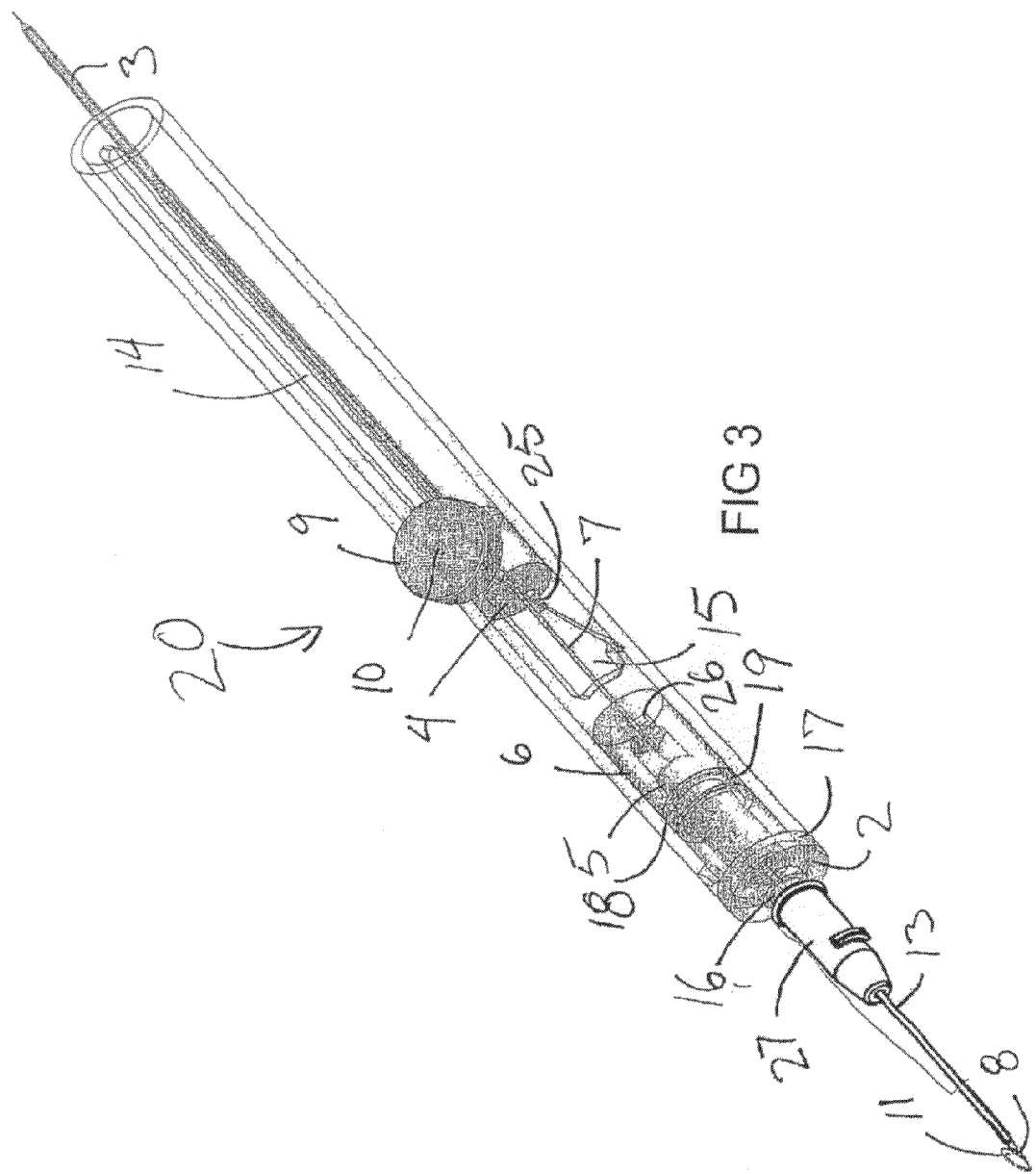
FIG. 3 shows a phantom view of the intravenous catheter insertion device with the safety guidewire advanced.

FIG. 1 shows an exploded view of one embodiment of an intravenous catheter insertion device 20 according to the present invention. FIG. 2 shows an assembly drawing of the intravenous catheter insertion device 20 in an undeployed state, ready for use. FIG. 3 shows a phantom view of the intravenous catheter insertion device 20 with the safety guidewire advanced.

The intravenous catheter insertion device 20 includes an outer housing 1. In the example shown, the outer housing 1 is in the form of an elongated hollow cylinder. Other shapes, including an ergonomic handle shape, are possible. The outer housing 1 may be formed from any material suited for use in medical applications. In one embodiment, the outer housing 1 is preferably molded from a rigid, transparent medical grade plastic. Alternatively, the outer housing 1 may be machined from an extruded plastic tube.

There is an elongated slot 14 in the outer housing 1 approximately parallel with the axis of the outer housing 1. The slot 14 is sized to accommodate the dowel pin 10 or provide a connection point to the slider 4 to move the slider along the interior of the outer housing 1. The distal end of the slot 14 widens into a triangular cutout 15, as seen in FIGS. 2 and 3. Other shapes of the cut out 15 are possible.

A front plug 2 is sized to fit onto the distal end of the outer housing 1. The front plug 2 is preferably molded, or alternatively machined, from a rigid, transparent medical grade plastic. The front plug 2 is glued, pinned, welded or otherwise fastened to the distal end of the outer housing 1. The distal end of the front plug 2 includes a luer slip fitting 16 or the like. There is a shoulder or flange 17 to mate with the distal end of the outer housing 1. The proximal end of the front plug 2 has an interlocking member 18 that interlocks with a mating interlocking member 19 on the needle carrier 6. In the example shown, the interlocking member 18 is a tab that interlocks with a corresponding spiral pawl or quarter-turn thread interlocking member 19 on the needle carrier 6. Other geometries for the interlocking members 18, 19 are possible.

In the exemplary embodiment of FIGS. 1-3, the geometry of the slot 14 and the triangular cutout 15 are chosen to operate cooperatively with the rotating interlocking members 18, 19. The slot 14 allows the actuator handle 9 to move in a longitudinal direction with respect to the outer housing 1 to advance the safety guidewire 11 distally, while at the same time restricting lateral motion to avoid premature withdrawal of the access needle 8 and the safety guidewire 11. The widening of the slot 14 at the distal end into a triangular cutout 15 allows the actuator handle 9 to be selectively rotated laterally to disengage the rotating interlocking members 18, 19 and release the biasing member 12 to withdrawal of the access needle 8 and the safety guidewire 11 after the the safety guidewire 11 has been fully advanced. If a different geometry or different release mechanism is used in place of the rotating interlocking members 18, 19, the geometry of the slot 14 and the triangular cutout 15 may have to be modified to accommodate the release mechanism.

The needle carrier 6 is shaped and sized to fit inside the outer housing 1. In the embodiment shown in FIGS. 1-3, the needle carrier 6 has a cylindrical shape that is sized to have a sliding fit within the cylindrical outer housing 1. Other shapes are possible and generally the needle carrier 6 will be shaped to be compatible with the interior geometry of the outer housing 1. The needle carrier 6 is preferably molded, or alternatively machined, from any material suited for use in a medical environment. In one embodiment, the needle carrier 6 is formed from a rigid, transparent medical grade plastic. A tubular access needle 8 with a sharpened beveled distal end is attached to a needle carrier nose 5, which is in turn attached to the needle carrier 6. The access needle 8 is preferably made from stainless steel hypodermic tubing. A small cavity or blood flashback chamber that communicates with the lumen of the access needle 8 is positioned within the needle carrier 6, between the needle carrier nose 5 and the needle carrier 6. As mentioned above, the distal end of the needle carrier 6 has an interlocking member 19 that is configured to interlock with a mating interlocking member 18 on the proximal end of the front plug 2. In one exemplary embodiment, the interlocking members 18, 19 are adapted to lock and unlock by rotation of the needle carrier 6 with respect to the front plug 2. The interlocking members 18,19 may also lock and unlock using a bayonet-type fitting. In the example shown, the interlocking member is a spiral pawl interlocking member 19 that interlocks with a corresponding tab interlocking member 18 on the front plug 2. In one embodiment, the interlocking members lock and/or unlock using less than one revolution of the needle carrier 6. In another embodiment, the interlocking members lock and/or unlock using less than one half a revolution of the needle carrier 6. In still another alternative embodiment, the interlocking members lock and/or unlock using less than one-quarter revolution of the needle carrier 6. Other geometries for the interlocking members are possible.

A biasing member 12 is configured to fit between the needle carrier 6 and the front plug 2 to urge them apart. The force of the biasing member 12 is resisted by the interlocking members 18, 19 when the needle carrier 6 and the front plug 2 are locked together. In one embodiment, the biasing member 12 is a spring. Note that in FIG. 1 the biasing member or compression spring 12 is shown in a compressed condition as it would be in the assembled intravenous catheter insertion device 20 in an undeployed condition.

In an alternate embodiment, the interlocking members 18, 19 may be replaced by two members that are bonded together with a breakable bond or a single member with a breakable link. The member or members would be configured to constrain the biasing member 12 until it is desired to withdraw the access needle 8 and safety guidewire 11, at which time, the actuator would break the bond or link to release the biasing member 12. This configuration would make the device 20 more resistant to remanufacturing or reuse.

A tubular intravenous catheter 13, such as an ANGIOCATH, fits coaxially around the access needle 8. Preferably, the intravenous catheter 13 has a close fit with the access needle 8 and a tapered distal end to minimize any step between the access needle 8 and the intravenous catheter 13 as they are inserted through the wall of a vein. There is a luer fitting 27 or the like on the proximal end of the intravenous catheter 13 that fits onto the luer slip fitting 16 on the distal end of the front plug 2 with a slight interference fit to hold the intravenous catheter 13 in place. Alternative configurations of the device may use a luer lock or other locking mechanism to attach the intravenous catheter 13 to the front plug 2.

A slider 4 is generally cylindrical in shape and sized for a sliding fit inside the cylindrical outer housing 1. Other shapes for the slider 4 are possible depending on the interior geometry of the outer housing 1. The slider 4 is preferably molded, or alternatively machined, from any suitable medical grade material. For example, the slider may be formed from a rigid medical grade plastic. A handle 9 or actuating member attaches to the slider 4 with a dowel pin 10 or other attachment member that extends through the slot 14 in the outer housing 1. The slider 4 fits into the outer housing 1 proximal to the needle carrier 6. A pin 25 extends from the distal surface of the slider 4 and is configured to reversibly engage with a hole, step, boss or similar mating feature 26 on the proximal end of the needle carrier 6. When pin 25 is coupled to the mating feature 26 during the appropriate step of the intravenous catheter insertion and placement procedure, rotation of the slider 4 is transferred to the needle carrier 6 to facilitate engagement and or disengagement of the interlocking members 18, 19. Pin 25 and feature 26 are merely illustrative. Pin 25 may be replaced with a female feature while a mating male feature may be placed on the proximal face of the needle carrier 6. Additionally, the mating features 25, 26 are aligned relative to the elongated slot and the sliding movement of the slider 4 so that distal movement of the slider 4 will engage the mating features 25,26. Optionally, the device 20 may be configured so that the connection between the slider 4 and needle carrier 6 happens irreversibly when the device 20 is actuated.

As best seen in FIG. 3, a safety guidewire 11 is attached, directly or indirectly, to the slider 4 so that it can be advanced and retracted with the handle 9 attached to the slider 4. In a preferred embodiment, the safety guidewire 11 is constructed of superelastic Nickel-Titanium alloy (Nitinol) wire. Because this type of wire is extremely flexible, it is advantageous to have the safety guidewire 11 enclosed along most of its length to avoid bowing or buckling while advancing the safety guidewire 11. For this reason, the example shown includes a support tubing 7 that is attached to the proximal end of the needle carrier 6. The safety guidewire 11 extends through the internal lumen of a sheath tubing 3 and the proximal end of the safety guidewire 11 is attached at the proximal end of the sheath tubing 3. The distal end of the sheath tubing 3 is in turn attached to the slider 4, indirectly attaching the safety guidewire 11 to the slider 4. The support tubing 7 has a sliding fit inside the sheath tubing 3 so that the two parts telescope together as the slider 4 is advanced in the distal direction. The telescoping action of the support tubing 7 and the sheath tubing 3 provides a variable-length support for the proximal portion of the safety guidewire 11 to prevent bowing or buckling of the safety guidewire 11 as it is advanced. The support tubing 7 and the sheath tubing 3 are preferably made from stainless steel hypodermic tubing, however any suitable medical grade plastic material may also be used. In other embodiments, such as those using a larger diameter or stiffer guidewire, the telescoping support tubes may not be necessary, and the proximal end of the safety guidewire 11 may be attached directly to the slider 4.

FIGS. 4A and 4B are detail drawings of a safety guidewire 11 for use with the intravenous catheter insertion device 20. The safety guidewire 11 is preferably constructed of superelastic Nickel-Titanium alloy wire approximately 0.004-0.012 inches in diameter and most preferably approximately 0.008 inches in diameter. As shown in FIG. 4B, the distal end of the safety guidewire 11 is preformed into a tightly wound spiral with an outer diameter smaller than the internal diameter of the target vessel into which it will be inserted. The spiral tip acts as a safety bumper on the guidewire to avoid puncturing or damaging the inside of target vessels. The coiled guidewire tip is particularly useful in protecting fragile or delicate veins. Due to the extreme flexibility of the Nickel-Titanium alloy wire, the spiral distal curve can straighten out when the safety guidewire 11 is withdrawn into the access needle 8 and completely recover into the spiral configuration without plastic deformation when the safety guidewire 11 is advanced out of the access needle 8. In the example shown, the distal end of the safety guidewire 11 has a first, small diameter coil of approximately 0.167 inches in diameter for approximately 0.75 revolutions and a second, larger diameter coil of approximately 0.175 inches in diameter for approximately 1 revolution. The first and second coils are preferably approximately coplanar with one another and preferably approximately coplanar with the straight proximal portion of the guidewire 11 also. Other configurations of the safety guidewire 11 may include: multi-planar, single coil, full radius on the end, and/or a balled end with diameter less than the diameter of the needle.

FIGS. 5A, 5B and 5C are detail drawings of another safety guidewire 11 for use with the intravenous catheter insertion device 20. In this embodiment, a distal portion of an approximately 0.008 inch diameter Nickel-Titanium alloy wire has been tapered by grinding, stretching, etc., to a diameter of approximately 0.004 inches to make it more flexible and to allow it to be formed into a smaller diameter spiral for use in smaller diameter veins. The spiral curve of the guidewire tip will preferably have an outer diameter smaller than the inner diameter of the target vessel. In the example shown, the spiral curve has a first, small diameter coil of approximately 0.034 inches in diameter for approximately 0.75 revolutions and a second, larger diameter coil of approximately 0.059 inches in diameter for approximately 1 revolution. The first and second coils are preferably approximately coplanar with one another and preferably approximately coplanar with the straight proximal portion of the guidewire 11 also.

Other sizes and geometries of safety guidewire 11 are also possible.

To assemble the intravenous catheter insertion device 20 shown in FIGS. 1-3, the access needle 8 is bonded flush with the proximal face of the needle carrier nose 5, which is in turn bonded into the needle carrier 6. The support tubing 3 is placed into the distal hole in the needle carrier 6, and bonded flush with the proximal face of the blood flashback chamber. The formed safety guidewire 11 is advanced through the lumen of the access needle 8 and support tubing 7 until the coiled section of the safety guidewire 11 meets the access needle 8 bevel. The sheath tubing 3 is slid through the slider 4, and bonded when flush with the distal face. The assembly of the sheath tubing 3 and slider 4 are advanced over the safety guidewire 11. When the safety guidewire 11 is flush with the proximal end of the sheath tubing 3, the two are bonded. The spring 12 is compressed on the needle carrier nose 5, advanced into the front plug 2 and the interlocking members 18, 19 of the front plug 2 and needle carrier 6 are engaged. This assembly of components is placed into the outer housing 1 and advanced until the front plug 2 is flush with the outer housing 1, and then the front plug 2 is rotated for proper alignment. The front plug 2 is then bonded to the outer housing 1. The dowel pin 10 and handle 9 are pressed together with the slider 4. The handle 9 is slid proximally to withdraw the safety guidewire 11 into the access needle 8, thereby straightening out the spiral distal curve. An intravenous catheter 13 is then mounted coaxially around the access needle 8. Optionally, the intravenous catheter 13 insertion device may be provided with a needle cover or other protective packaging. The assembled intravenous catheter insertion device 20, including the intravenous catheter 13, is then packaged, labeled and sterilized.

The preceding assembly description is provided to illustrate one example of a process for manufacturing an embodiment of the intravenous catheter insertion device 20 and also so that the interrelationship of the various components will be understood. Modifications and variations of this description are expected depending upon specific selected assembly or manufacturing techniques. For example, components that are bonded may be redesigned to be formed from a single integrated piece and the like. The manufacturing process can be modified and adapted for assembling other embodiments of the intravenous catheter insertion device 20.

Figure 6:
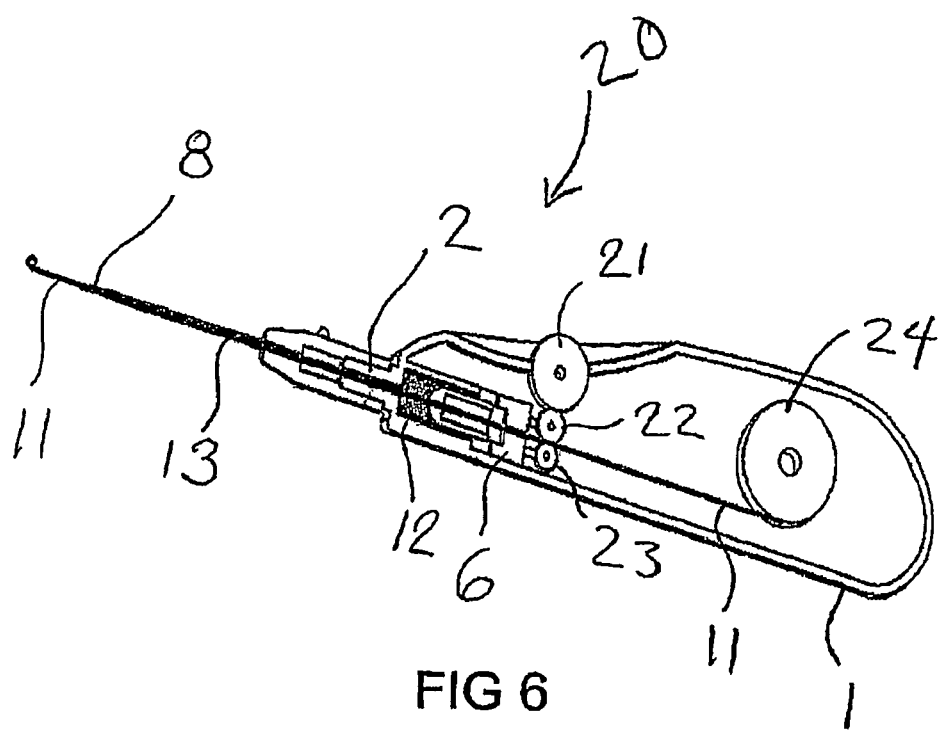
FIG. 6 shows another embodiment of an intravenous catheter insertion device according to the present invention.

FIG. 6 shows an interior view of another embodiment of an intravenous catheter insertion device 20 according to the present invention. This embodiment is similar in many respects to the intravenous catheter insertion device 20 of FIGS. 1-3. The intravenous catheter insertion device 20 includes an outer housing 1, front plug 2, which may optionally be molded integrally with the outer housing 1, a needle 8 attached to a needle carrier 6, a safety guidewire 11, spring 12 and intravenous catheter 13. However, the functions of the handle 9 and the slider 4 have been replaced by a thumbwheel 21 that engages a pair of friction wheels 22, 23, which are in contact with the safety guidewire 11. Likewise, the functions of the sheath tubing 3 and the support tubing 7 have been replaced by a guidewire spool 24. These features allow the intravenous catheter insertion device 20 to be constructed in a more compact configuration. In use, the safety guidewire 11 is advanced by turning the thumbwheel 21. A lateral movement of the thumbwheel 21 disengages the needle carrier 6 from the front plug 2, allowing the biasing member 12 to expand, thereby retracting the needle 8 and the safety guidewire 11 into the outer housing 1. Alternatively, a separate button, lever or other actuation member can be provided to actuate the withdrawal of the needle 8 and the safety guidewire 11. The guidewire spool 24 may optionally include a rotary spring or similar mechanism (not shown) to assist in the retraction of the safety guidewire 11 into the outer housing 1.

Figure 7:
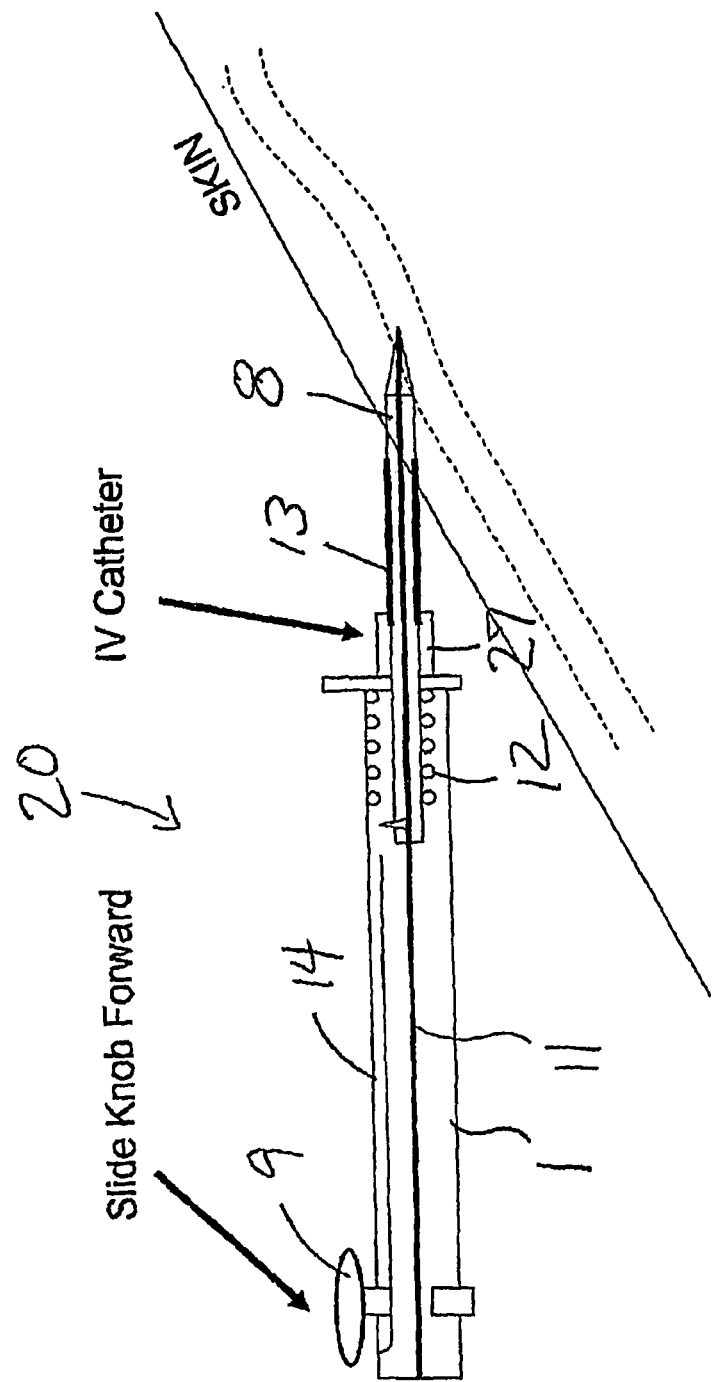
Figure 8:
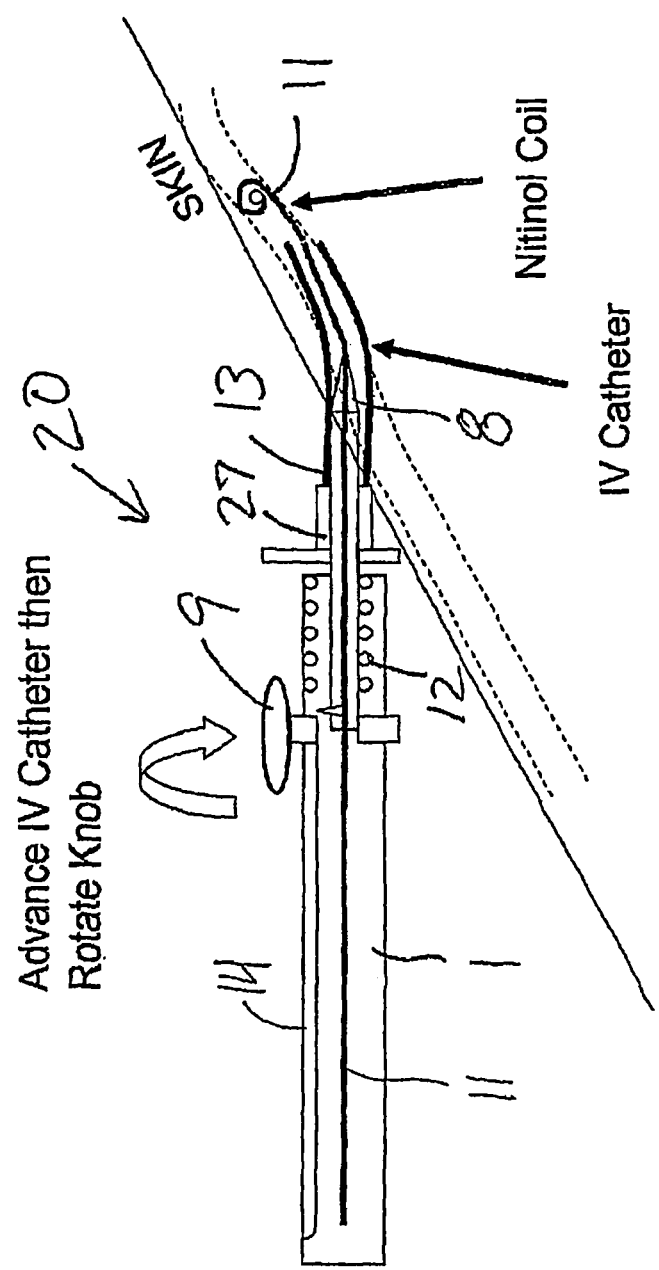

FIGS. 7-9 illustrate a method of inserting an intravenous catheter using an intravenous catheter insertion device 20, such as those described in FIGS. 1-3 or FIG. 6. The intravenous catheter insertion device 20 is a single-use, non-reusable device supplied to the physician or medical practitioner sterile in a ready-to-use, undeployed condition as shown in FIG. 2. In use, the physician uses the outer housing 1 as a handle to manipulate the intravenous catheter insertion device 20. With the device in the undeployed condition, the access needle 8 is used to puncture a vein, as shown in FIG. 7. When venous blood is observed in the blood flashback chamber, the distal tip of the access needle 8 is the lumen of the vein. The physician can then advance the handle 9 in the distal direction to extend the safety guidewire 11 out of the access needle 8 into the lumen of the vein. The distal portion of the safety guidewire 11 assumes its spiral configuration to act as a safety bumper to prevent accidental puncture of the far wall of the vein or other damage to the vein. With the safety guidewire 11 thus deployed, the physician can safely continue advancing the intravenous catheter insertion device 20 until the distal tip of the intravenous catheter 13 is in the lumen of the vein. Once the intravenous catheter 13 is inserted far enough into the vein, the physician rotates the handle 9 that rotates the slider 4, which in turn rotates the needle carrier 6 and disengages the interlocking member 18 of the needle carrier 6 from the mating interlocking member 19 on the front plug 2. (In the exemplary embodiment described above, the handle moves in a counterclockwise direction as allowed by the triangular cutout 15 at the distal end of the slot 14 in the outer housing 1. Additional structural features of the actuator mechanism are shown in more detail in FIGS. 1-3.) When the handle 9 is released, the biasing element (here a compression spring 12)

urges the needle carrier 6 and the slider 4 in the proximal direction, thus simultaneously withdrawing the access needle 8 and the safety guidewire 11 into the outer housing 1, leaving only the intravenous catheter 13 in the lumen of the vein. FIG. 8 shows the access needle 8 and the safety guidewire 11 withdrawing into the outer housing 1. The shape of the triangular cutout 15 allows the handle 9 to make a smooth transition into the elongated slot 14 as it moves proximally under the influence of the biasing element 12. Finally, the intravenous catheter 13 is disengaged from the luer slip 16 fitting on the distal end of the front plug 2, as shown in FIG. 9, and a source of intravenous fluid, a syringe or other device is attached to the luer fitting 27 of the intravenous catheter 13.

While it is desirable for the intravenous catheter insertion device 20 to withdraw the access needle 8 and the safety guidewire 11 simultaneously, the actuator mechanism could also be modified to withdraw the access needle 8 and the safety guidewire 11 sequentially. For example, the actuator mechanism could withdraw the access needle 8 first and then, after a slight delay, withdraw the safety guidewire 11.

Alternatively, the actuator mechanism could be modified to require two separate motions of one actuator member or selective movements of two separate actuator members to withdraw the access needle 8 and the safety guidewire 11 selectively.

In an alternative embodiment of the intravenous catheter insertion device 20, the compression spring 12 may be omitted from the actuator mechanism, thus allowing the access needle 8 and the safety guidewire 11 to be withdrawn manually using the handle 9. Once the intravenous catheter 13 has been inserted into the patient's vein, the handle 9 is rotated laterally to disengage the needle carrier 6 from the front plug 2, then the handle 9 is moved proximally along the slot 14 to withdraw the access needle 8 and the safety guidewire 11 into the outer housing 1.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof. For example, all dimensions and materials included in the specification or drawings are intended only as examples of presently preferred embodiments and are not intended to limit the scope of the invention.

We claim:

1. A catheter insertion device, comprising:
    an outer housing; having a first end and a second end;
    a tubular access needle attached to a needle carrier, wherein said needle carrier is initially fully advanced in a distal direction but slidable in a proximal direction with respect to said outer housing;
    a tubular catheter releasably attached at a distal end of said outer housing and positioned coaxially around said tubular access needle;
    a safety guidewire sized and configured to be advanced through said tubular access needle, wherein the safety guidewire is initially fully retracted in a proximal direction relative to said outer housing;
    an actuator mechanism configured to selectively advance said safety guidewire out through said tubular access needle in a distal direction and subsequently to simultaneously withdraw said safety guidewire and said tubular access needle in a proximal direction with respect to said tubular catheter, said actuator mechanism comprising a compression spring located at a distal end of the outer housing coaxially over the tubular access needle and safety guidewire and an interlock attached at the first end to the needle and at the second end to the outer housing, which interlock can be selectively released to allow the compression spring to elongate to simultaneously withdraw said safety guidewire and said tubular access needle.

2. The catheter insertion device of claim 1, further comprising:
    an actuator handle configured to move distally with respect to said outer housing to selectively advance said safety guidewire out through said tubular access needle in a distal direction, wherein said actuator handle is configured to rotate laterally to disengage said interlock to release the needle from the outer housing and allow withdrawal of said safety guidewire and said tubular access needle in a proximal direction with respect to said tubular catheter.

3. The catheter insertion device of claim 1, further comprising:
    an elongated slot in said outer housing, said elongated slot having a narrow proximal portion and a widened distal portion; and
    an actuator handle is movable with respect to said elongated slot, such that said narrow proximal portion of said elongated slot constrains said actuator handle to move in a longitudinal direction to selectively advance said safety guidewire out through said tubular access needle in a distal direction and said widened distal portion allows said actuator handle to move in a lateral direction to actuate withdrawal of said safety guidewire and said tubular access needle in a proximal direction with respect to said tubular catheter.

4. The catheter insertion device of claim 3, wherein said interlock comprises a front plug affixed to said distal end of said outer housing, said front plug having a proximal end with a tab that rotatably interlocks with a spiral pawl on a distal end of said needle carrier;
    wherein said spring is compressed between said front plug and said needle carrier; and
    wherein the lateral movement of said actuator handle rotates said needle carrier thereby releasing said needle carrier from said front plug and allowing said spring to urge said needle carrier in a proximal direction with respect to said outer housing.

5. The catheter insertion device of claim 4, wherein said front plug further comprises a distal end having a luer slip fitting for releasable attaching said tubular catheter to said front plug.

6. The catheter insertion device of claim 4, wherein said actuator mechanism comprises:
    a slider located within said outer housing, said slider connected to said actuator handle, said slider having a distal end with a projection configured to engage said needle carrier and to transfer rotation of said slider to said needle carrier to release said needle carrier from said front plug.

7. The catheter insertion device of claim 6, wherein:
    said safety guidewire is connected to said slider.

8. The catheter insertion device of claim 1, further comprising:
    a thumbwheel configured to rotate with respect to said outer housing to selectively advance said safety guidewire out through said tubular access needle in a distal direction.

9. The catheter insertion device of claim 1, wherein said safety guidewire has a distal portion formed into a spiral curve.

10. The catheter insertion device of claim 9, wherein said spiral curve of said safety guidewire comprises a first spiral rotation and a second spiral rotation, said first spiral rotation being of a smaller diameter than said second spiral rotation.

11. The catheter insertion device of claim 10, wherein said first spiral rotation of said spiral curve of said safety guidewire is approximately coplanar with said second spiral rotation.

12. The catheter insertion device of claim 1, wherein said safety guidewire comprises a proximal portion and a distal portion, said proximal portion having a diameter that is greater than a diameter of said distal portion.

13. The catheter insertion device of claim 12, wherein said distal portion of said safety guidewire is formed into a spiral curve.

14. The catheter insertion device of claim, wherein said safety guidewire is formed from a superelastic Nickel-Titanium alloy.

15. A method for inserting a catheter into a patient, comprising:
providing a catheter insertion device comprising an outer housing, a tubular access needle attached to a needle carrier, an interlock attached at a first end to the needle carrier and at the second end to said outer housing, a tubular catheter releasably attached at a distal end of said outer housing and positioned coaxially around said tubular access needle, a safety guidewire sized and configured to be advanced through said tubular access needle, and an actuator mechanism having a handle coupled to the safety guidewire and a compressed spring disposed coaxially over a proximal portion of the tubular access needle and the safety guidewire;
inserting a distal end of said tubular access needle into the patient;
actuating the said actuator mechanism to advance said safety guidewire out through said tubular access needle in a distal direction;
disengaging the tubular catheter from the outer housing;
advancing a distal end of said tubular catheter over the tubular access needle and the safety guidewire into the patient; and
actuating the handle of said actuator mechanism to disengage the interlock to release the needle carrier from the outer housing which allows the compressed spring to expand and engage the needle carrier and the safety guidewire to simultaneously withdraw said safety guidewire and said tubular access needle in a proximal direction with respect to said tubular catheter.

16. The method of claim 15, further comprising:
releasing said tubular catheter from said distal end of said outer housing.

17. The method of claim 15, wherein the interlock comprises a pair of interlocking members wherein a first interlocking member is disposed within said outer housing and is engaged with a mating interlocking member of said needle carrier; wherein said compressed spring is constrained by the engagement of said first interlocking member with said mating interlocking member; and wherein said actuator mechanism is actuated to disengage said mating interlocking member from said first interlocking member, thus releasing said compressed spring to urge said needle carrier in a proximal direction with respect to said outer housing.

18. The method of claim 15, further comprising:
moving an actuator handle distally with respect to said outer housing to selectively advance said safety guidewire out through said tubular access needle in a distal direction; and
moving said actuator handle laterally to release said compressed spring to initiate withdrawal of said safety guidewire and said tubular access needle in a proximal direction with respect to said tubular catheter.

19. The method of claim 15, wherein a distal portion of said safety guidewire is initially constrained in a straightened configuration within said tubular access needle; and wherein said distal portion of said safety guidewire assumes a spiral curve configuration upon advancement of said safety guidewire though said tubular access needle in a distal direction.

20. The method of claim 15, further comprising:
rotating a thumbwheel with respect to said outer housing to selectively advance said safety guidewire through said tubular access needle in a distal direction.

* * * * *